US007608270B2

(12) United States Patent
Beckett et al.

(10) Patent No.: US 7,608,270 B2
(45) Date of Patent: Oct. 27, 2009

(54) DOSAGE FORM

(75) Inventors: Stephen Thomas Beckett, York (GB); Stephen Lawrence Atkin, Hessle (GB); Grahame Mackenzie, Hull (GB)

(73) Assignee: University of Hull, Hull (GB)

( * ) Notice: Subject to any disclaimer, the term of this patent is extended or adjusted under 35 U.S.C. 154(b) by 259 days.

(21) Appl. No.: 10/877,042

(22) Filed: Jun. 25, 2004

(65) Prior Publication Data
US 2005/0002963 A1    Jan. 6, 2005

Related U.S. Application Data

(60) Provisional application No. 60/482,922, filed on Jun. 27, 2003.

(51) Int. Cl.
*A61K 36/00*    (2006.01)
(52) U.S. Cl. .................. 424/195.15; 424/195.17; 424/725; 424/780; 424/275.1
(58) Field of Classification Search .............. None
See application file for complete search history.

(56) References Cited

U.S. PATENT DOCUMENTS

| | | | |
|---|---|---|---|
| 5,013,552 A | 5/1991 | Samir Amer et al. |
| 5,275,819 A | 1/1994 | Amer et al. |
| 5,648,101 A | 7/1997 | Tawashi |
| 6,156,330 A | 12/2000 | Shirata et al. |

FOREIGN PATENT DOCUMENTS

| | | |
|---|---|---|
| CN | 1105594 | 7/1995 |
| DE | 19902724 | 7/2003 |
| WO | WO 99/49063 | 9/1999 |
| WO | WO 02/055561 A1 | 7/2002 |
| WO | WO 03078048 A2 | 9/2003 |
| WO | WO 03/094942 A1 | 11/2003 |
| WO | WO 2005/000280 A3 | 1/2005 |

OTHER PUBLICATIONS

Ivleva et al. (Analytical and Bioanalytical Chemistry (2005), vol. 381, No. 1, pp. 261-267).*
International Search Report dated Apr. 25, 2005 from related International Application No. PCT/GB2004/002775.
Hamilton, et al., "Survey for Prunus Necrotic Ringspot and Other Viruses Contaminating the Exine of Pollen Collected by Bees," Canadian Journal of Plant Pathology, vol. 6, No. 3, 1984, pp. 196-199.
Shaw et al., "The Use of Modified Sporopollenin From Lycopodium clavatum As a Novel Ion- or Lignand-Exchange Medium," Reactive Polymers, vol. 9, No. 2, Nov. 1, 1988, pp. 211-217.
Ahlers et al., "The Nature of Oxygen in Sporopollenim from the Pollen of Typha angustifolia L.," Journal of Biosciences, 200 Mar.-Apr., vol. 55, No. 3-4, pp. 129-136.

Adamson et al., "New applications of sporopollenin as a solid phase support for peptide synthesis and the use of sonic agitation," International Journal of Peptide and Protein Research, Nov. 1983, vol. 22, No. 5, pp. 560-564.
Hamilton, et al., "Survey for Prunus Necrotic Ringspot and Other Viruses Contaminating the Exine of Pollen Collected by Bees," Canadian Journal of Plant Pathology, vol. 6, No. 3, 1984, pp. 196-199, abstract only.
"Bioavailability of orally delivered therapeutics: a biological perspective", dds&s, vol. 2, No. 4, Dec. 2002/Jan. 2003, pp. 100-102.
Andy Clark, "Formulation of proteins and peptides for inhalation", dds&s, vol. 2, No. 3, Sep./Oct. 2002, pp. 73-77.
Ian Smith, "Bioavailability, targeting and controlled release—the key to effective drug delivery?", dds&s, vol. 2, No. 4, Dec. 2002/Jan. 2003, p. 89.
Gregory Gregoriadis, "Lipsomes in drug and vaccine delivery", dds &s, vol. 2, No. 4, Dec. 2002/Jan. 2003, pp. 91-97.
Reslow et al., "Sustained-release of human growth hormone from PLG-coated starch microspheres", dds&s, vol. 2, No. 4, Dec. 2002/Jan. 2003, pp. 103-109.
Crockford et al., "Adaptive Aerosol Delivery (AAD™) technology: drug delivery technology that adapts to the patient", dds&s, vol. 2, No. 4, Dec. 2002/Jan. 2003, pp. 110-113.
Alan Wiseman, "Targeted membrane-penetrating peptides: identify candidate drug-cargoes in silico?", dds&s, vol. 2, No. 4, Dec. 2002/Jan. 2003, p. 114.
Alan Wiseman, "Cell-Penetrating Petides. Processes and Applications", dds&s, Vol. 2, No. 4, Dec. 2002/Jan. 2003, p. 115.
Wittborn et al., "Nanoscale Similarties in the Substructure of the Exines of *Fagus* Pollen Grains and *Lycopodium* Spores", Annals of Botany 82: pp. 141-145, 1998.
M.L. Weiner, "Intestinal Transport of Some Macromolecules in Food", Fd Chem. Toxic, vol. 26, No. 10, pp. 867-880, 1998.
Bohne et al., "Diffusion Barriers of Tripartite Sporopollenin Microcapsules Prepared from Pine Pollen", Annals of Botany 92: pp. 289-297, 2003.
Fenyvesi et al., "Synthesis and characterization of tubular amphiphilic networks with controlled pore dimensions for insulin delivery", http://wost.wok.mimas.ac.uk:8000/CIW.cgi., Feb. 17, 2004.
Polysciences, Inc., "Sporopollenin Microparticles", Technical Data Sheet 281, Oct. 1999, pp. 1-2.
Jorde et al., "ZUR Persorption Von Pollen UND Sporen Durch Die Intake Darmschleimhuat", Acta Allergologica, 1974, 29, 165-175.
Volkheimer et al., "Le phénomène de la Persorption et son importance en Allergologie", Maroc. Med., (1967), 47, 626-633.
Pollen: Biology, Biochemistry Management, R. G. Stanley, H. F. Linskens (New York, Springer-Verlag, 1974), pp. 114-115, 179-181.

* cited by examiner

*Primary Examiner*—Susan C Hoffman
(74) *Attorney, Agent, or Firm*—Weaver Austin Willeneuve & Sampson LLP; Emily M. Haliday

(57) ABSTRACT

A pharmaceutical or dietetic dosage form comprising of effective quantity of an active substance chemically or physically bound to a support comprising sporopollenin, or other similar exine coating of spores, of a plant or fungus, optionally with further excipients.

Figure 1:
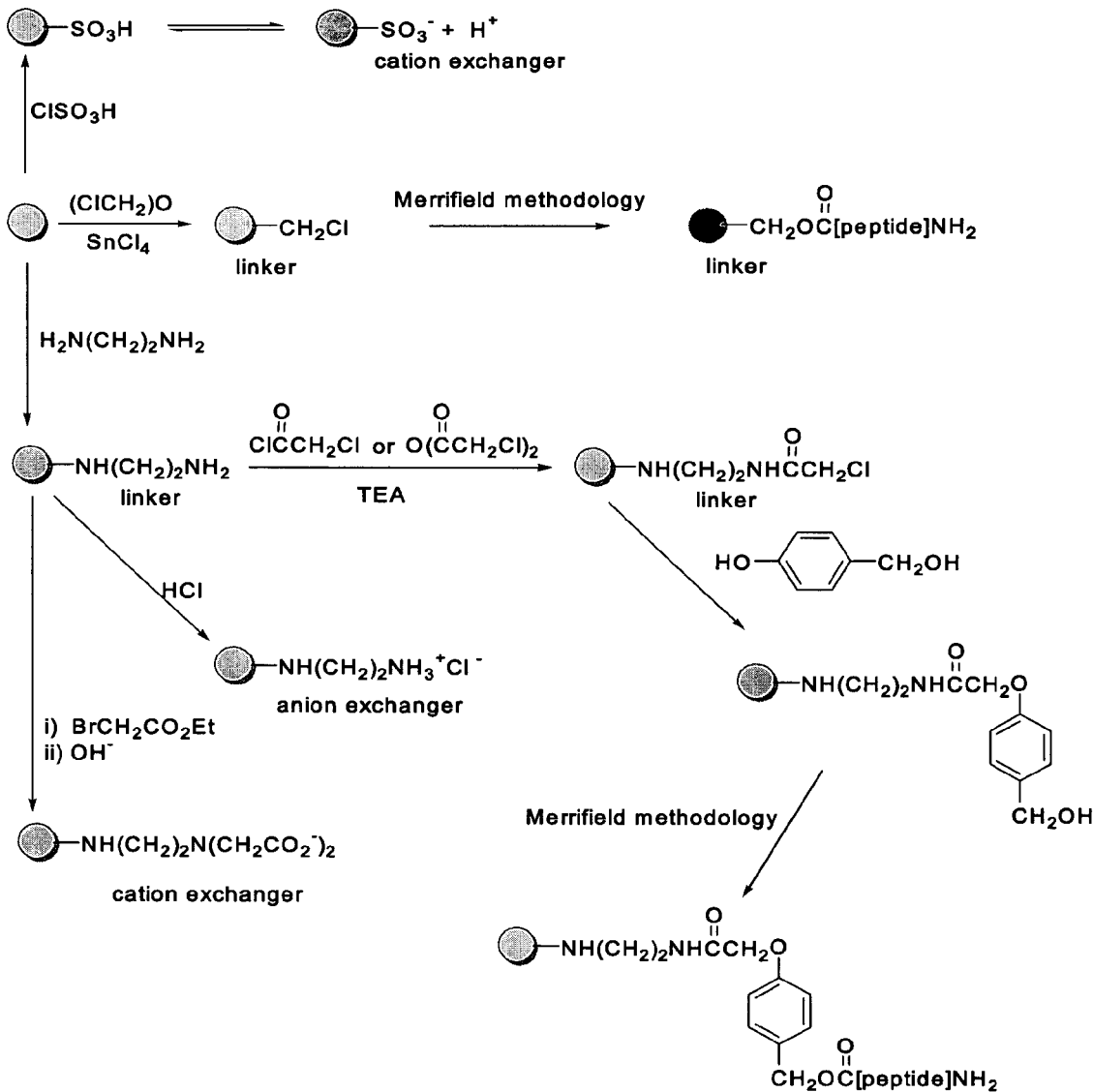

82 Claims, 9 Drawing Sheets cisplatin            CBDCA

JM-40            'sporoplatin'

DOSAGE FORM

This application claims priority to U.S. Provisional Patent Application No. 60/482,922 filed Jun. 27, 2003, titled DOSAGE FORM; the disclosure of which is incorporated herein by reference in the entirety and for all purposes.

This invention relates to a pharmaceutical/dietetic dosage form, a method of manufacture of such a dosage form and methods of treatment using the dosage form. Dosage forms for human and veterinary use are provided.

Sporopollenins are the exine coatings of spores of various plants, mosses, fungi and algae. Sporopollenins may be separated from spores by successive treatment with solvents, alkali and acid to remove the lipid, carbohydrate, protein and nucleic acids, which may be attached to or contained within the sporopollenin exine coating. Enzymic methods have also been used. Sporopollenins are chemically and physically stable, and have been described as being carotenoid-like and being hydrophobic. Other exine coatings made glucans, mannans and chitin can have similar chemical and physical stability. Some spores however have intine coatings which are partly made up of cellulose; the intine would be largely degraded by such chemical treatment (F. Zetzsche and K. Huggler *Annalen*, 1928, 461, 89)).

DE-A-19902724 discloses a dosage form wherein microcapsules are produced from sporopollenin capsules filled with active substances. Such a dosage form has the disadvantage that the release of the active substance or substances, is dependent on the integrity of the capsule. Unlike this disclosure the current invention makes use of both the elastic nature and the presence of alcohol to aid the filling of the sporopollenin sac, particularly to increase the processing rate, and the use of specific exine coating size to target delivery.

U.S. Pat. No. 5,013,552 discloses use of loaded cellulose shells obtained from pollen grains for delivery systems. Such a shell is like the intine in that it would be destroyed by the extraction procedure used to obtain the sporopollenin.

According to a first aspect of the present invention a pharmaceutical or dietetic dosage form comprises an effective quantity of an active substance chemically bound to a support selected from an exine coating of spores of a plant, moss, fungus, or algae, or fragment thereof, optionally with further excipients.

According to a second aspect of the present invention a pharmaceutical or dietetic dosage form comprises an effective quantity on an active substance physically bound within a support selected from an exine coating of spores of a plant, moss, fungus or algae, or fragments thereof, optionally with further excipients.

The active substance when physically bound may be adsorbed on to the support.

Alternatively and often more preferably the active substance is retained within the cavities that are integral to the sporopollenin wall of the hollow exine coatings e.g. sporopollenins or within the central cavity. All three aspects enable administration by absorption of the dosage form into the bloodstream followed by degradation of the coatings to liberate the active substance.

According to a third aspect of the present invention a method of making a pharmaceutical or dietetic dosage form comprises the steps of:

contacting an exine coating with a penetration aiding liquid contacting the exine coating with an active substance and allowing the substance to penetrate into the cavities of the sporopollenin wall and/or contacting the exine coating with an active substance and allowing the substance to penetrate into the interior of an exine coating, and subsequently removing the penetrating aiding liquid and allowing the exine coating to dry to retain the substance within the coating.

A preferred penetration aiding liquid may be a solvent or solubilising agent selected from the group consisting of: $C_1$ to $C_4$ alcohols more preferably ethanol and aqueous $C_1$ to $C_4$ alcohols preferably aqueous ethanol.

The sporopollenin exine coating may be soaked in a solution of the active substance in the liquid. Alternatively, the coating may be soaked in the solvent or other penetration aiding liquid prior to contacting with the active substance.

The sporopollenin exine coating may be: (i) pressurised to form tablets which are then put into contact with a solution of the active substance (or simply the active substance in liquid form with or without the penetration aiding liquid) either at atmospheric pressure or under vacuum; (ii) subjected to a vacuum in presence of the active substance with or without the penetration aiding liquid. These procedures may be operated at ambient temperature or elevated temperatures up to 250° C. The active substance may comprise a drug, a mixture of drugs, a dietetic substance, a mixture of dietetic substances or a mixture of drugs and a dietetic substance. Examples of dietetic substances include minerals and essential oils. Cholesterol lowering dosage forms may be provided. Vitamins, minerals, food flavourings and other nutraceutical active substances may be administered using a dosage form in accordance with the invention.

Dosage forms in accordance with this aspect of the invention may be incorporated into foodstuffs, for example cholesterol lowering food stuffs such as cereal bars. Veterinary dietetic products may be provided.

High loadings of the active substances may be achieved, for example several times the weight of the exine coating. This ability to encapsulate relatively large amounts of other materials facilitates addition of nutraceutical or other ingredients or additives such as flavours, preservatives, antioxidants or minerals to other products such as foods and drinks. The sporopollenin exine may provide protection for the active substance against moisture, acidity, alkalinity oxidation or photolytic degradation until the product is consumed. Some substances e.g. copper sulphate, are not readily released into aqueous solution, whereas others (which are only physically contained) are slowly released. The attachment of copper sulphate was shown SEM-X-ray to be evenly absorbed throughout the sporopollenin shells. The active ingredient may be slowly released as it is transported through the gut. Where this is undesirable an additional coating can be put on the sporopollenin exine coating to delay release. The exine coating may be derivatised to reduce its semipermability, for example using a low viscosity resin such as gum arabic. If absorption into the blood stream is undesirable, larger particles of sporopollenin (>100 microns) may be used.

In preferred dosage forms the exine coating comprises sporopollenin, glucans, mannans or chitin. These exine coatings have the advantages that they are chemically and mechanically stable, are convenient to use and administer and are easy and cheap to prepare. They may be generally free of leachable impurities and may be functionalised to provide a high active substance loading capability and have the advantage of an absence of protein, avoiding allergenic or other physiological effects due to traces of protein or denatured protein. The latter would be present in a less stringent extraction procedure such as is described in U.S. Pat. No. 5,013,552.

In preferred embodiments of the invention the support consists essentially of an exine coating comprising sporopollenin, chitin, glucans or mannans substantially in the absence of protein.

An amount of protein less than 0.5%, preferably less than 0.1% is particularly preferred.

Preferred coatings contain a sufficiently low level of protein that further loss of protein is not observed following reflux for 2 hours in 6% $^{W}/_{V}$ aqueous potassium hydroxide.

A dosage form in accordance with this invention has the advantage that it may be stable in acid or alkaline media but be rapidly biodegradable in certain circumstances, particularly in the blood. The degradation products may be non-toxic and may not show an inflammatory response. Residence time in the gastrointestinal tract may be low. Degradation may occur rapidly within the bloodstream and perhaps to a lesser extent in the gastrointestinal tract, permitting efficient and rapid administration of the drug or active substance, for example within a period of a few minutes, e.g. 20.

Accordingly, in one embodiment, the invention provides a method of oral delivery of an active ingredient using an insoluble vector (support) into the bloodstream wherein the active ingredient reaches the bloodstream in less than 20 minutes and the vector is then degraded within 3 hours.

The dosage form may comprise a bioconjugate, that is a macromolecular complex obtained synthetically by chemically bonding, e.g. covalently bonding drug molecules to a carrier or substrate comprising a, sporopollenin or other exine coatings. Although covalent bonding is preferred for same applications, ionic bonding, hydrogen bonding, van der Vaals forces or encapsulation within the exine coating may be used, particularly in applications such as for inhalation formulations in which strong bonding of the drug or other active substance to the carrier may not be required. The active substance or drug may be reacted directly with the sporopollenin or physically attached to produce a bioconjugate. However, in embodiments of this invention the sporopollenin or other exine coating is functionalised so that the drug can be attached by a suitably stable covalent linkage or other chemical linkage. For example, for oral delivery the linkage may be selected to be stable in acid solutions so that the active substance and support can pass through the stomach into the intestinal tract. Alternatively, drugs which are encapsulated may be stabilised due to protection provided by the exine coating. Added protection of physically attached or chemically attached active substances may be achieved by an additional coating such as with gum arabic or starch. Conventional film coatings may be used, for example, hydroxypropyl cellulose or other modified celluloses.

Dosage forms in accordance with this information find particular application in administration of drugs, which are labile in aqueous or especially in acid media for example, β-lactams, cephalosporins or dideoxyadenosine. Decomposition before release into the blood may be reduced. Administration of insoluble or poorly soluble drugs such as cyclosporins, taxanes, or other macrolides into the blood stream is also facilitated for example, ciclosporin, mebendazole, nystatin, propofol, paclitaxel, miconazole anthracyclinones or ciprofloacin.

Supports consisting of or comprising sporopollenin or other exine coating have distinct advantages over commercial polymers which have been used to deliver drugs or other active substances on account of the ability to persorb rapidly into the blood following oral administration and their ability to be rapidly catabolised (20 min to 2 h). In addition they can be readily derivatised to attach a wide range of drugs, having different solubilities and stabilities. Such a support may be chemically and morphologically consistent depending on its biological origin, may be capable of protecting acid labile molecules and is non-toxic. Also, there is no allergic response when sporopollenin or other exine coatings are taken orally by mouth or by inhalation into the lungs in part due to the proteins and carbohydrate associated with such responses having been removed from the raw plant spore. Decomposition of sporopollenin or exine coating occurs rapidly in blood allowing a quick release of the active ingredient. Such coating may retain their size and morphology during administration and absorption. Uniformity of size and morphology of the exine coatings from particular species enables the dosage form to be optimised in accordance with the drug loading and mode of delivery. Larger particles may contain a higher proportion of active materials such as drugs or functional food ingredients. We have found it possible for 25 micron particles to hold more than an equal weight of active material, within a central cavity. It has previously been suggested that such large particles cannot persorb through the gut wall into the blood stream (M L Wierner, Fd Chem. Toxic., 1988, 26(10)867-880).

There are numerous papers, reviews and books dealing with the subject of bioconjugation (two notable citations include: Bioconjugate Techniques, Greg T Hermanson, 1996, Academic Press Inc and Bioconjugation in Pharmaceutical Chemistry, Il Farmaco, 1999, 54, 497-526). Many coupling agents are disclosed. Carbodiimides such as DCC (dicyclohexylcarbodiimide) or EDC {1-ethyl-3-(3-dimethylaminopropyl)carbodiimide hydrochloride} are highly effective. Some drugs and probes incorporating either primary amine or carboxylate groups can be coupled directly to underivatised sporopollenin.

A dosage form in accordance with the present invention may be administered alone, particularly for inhalation administration but generally at least one suitable pharmaceutical excipient, diluent or carrier may be selected with regard to the intended route of administration.

The dosage form may be adapted for administration orally, buccally or sublingually in the form of tablets, capsules, including soft gel capsules, ovules, elixirs solutions or suspensions. The dosage form may be adapted for immediate, delayed, modified or controlled release delivery. Use of exine coatings in compressed formulations is sometimes advantageous because they have elastic properties maintaining integrity during tabletting and enabling tablet size to be reduced if necessary.

The dosage form may also be adapted for fast dispersing or fast dissolving administration.

Compressed tablets or other compressed dosage forms may be employed. Aqueous and non-aqueous coatings may be applied. Alternatively, formulations may incorporate a disintegrant or effervescent couple to facilitate dispersion in a liquid.

Tablets in accordance with the invention may contain excipients such as microcrystalline cellulose, lactose, sodium citrate, calcium carbonate, dibasic calcium phosphate, glycine and starch, preferably corn, potato or tapioca starch, disintegrants such as sodium starch glycollate, croscarmelose sodium and granulation binders such polyvinylpyrollidone, hydroxypropylmethylcellulose, hydroxypropyl cellulose, methylcellulose, sucrose and gelatin. Lubricants such as magnesium stearate and glidants such as talc or colloidal silica may be used.

Dosage forms in accordance with this invention may be employed as fillers in gelatin capsules. Preferred excipients include lactose, co-crystalline sugars, starch, cellulose and polyethylene glycols. Alternatively, freeze dried dosage forms may be used, for example as disclosed in GB 1548022 and various patents relating to the Zydis (TM) formulations of RP Scherer Corp.

Dosage forms in accordance with this invention may comprise aqueous suspensions or dried granules or other compositions for reconstitution as suspensions.

Modified release or pulsatile release dosage forms may contain release rate modifiers including hydroxypropyl methyl cellulose, methyl cellulose, sodium carboxymethyl cellulose, ethyl cellulose, cellulose acetate, polyethylene oxide, xanthan gum, Carbomers, oils and waxes and methacrylate co-polymers.

Transdermal administration may also be employed, particularly using small sporopollenin fragments.

In particularly preferred embodiments the dosage forms of this invention are adapted for pulmonary administration. The sporopollenin or other exine coatings may be selected from a moss, fungal or plant species to provide particles with a dimension selected to allow the dosage form to penetrate to the desired site of administration, for example, the lower lung. A particle size of about 1-100 microns, preferably about 1-30 microns, more preferably about 1-10 microns especially 1-5 microns is particularly preferred.

A dosage form in accordance with this aspect of the invention may have the advantage of uniformity of particle size. Furthermore, the largely unchanged size and shape of particles are after extraction of the spores using acids, bases or organic solvents. The extracted exine coating may retain similar size and shape to that of the spore from which it is derived. In contrast, micronised drugs such as are conventionally used for asthma treatment exhibit a range of particle sizes including a proportion of very fine particles and larger agglomerates.

Spores from a particular species have a narrow size distribution and consistent shape for each species and may be selected to provide a dosage form suitable for a selected site or mode of administration. Spores useful in accordance with this invention may be obtained from gymnosperms, angiosperms, pteridosperms, fungi and algae, in accordance with the disclosures of the following publications, which are incorporated with this specification by reference:

G. Shaw, Sporopollenin in Phytochemical Phylogeny, J. B. Harbome (Ed), Academic press, London and New York, Chapter 3, (1997), 31-5.

P. D. Moore, J. A. Webb and M. E. Collinson, Pollen analysis, 2nd edition, Blackwell Scientific Publications, (1999).

J. Brooks, Some Chemical and Geochemical Studies on Sporopollenin in: Sporopollenin, J. Brooks, M. Muir, P. Van Gijzel and G. Shaw, (Eds) Academic press, London and New York, (1971), 305-348.

Spore sizes for representative species are as follows:

Examples of Spore Sizes

| | |
|---|---|
| *Bacillus subtilis* | 1.2 μm |
| *Myosotis* (Forgetmenot) | 2.4-5 μm |
| *Aspergillus niger* | 4 μm |
| *Penicillium* | 3-5 μm |
| *Cantharellus minor* | 4-6 μm |
| *Ganomerma* | 5-6.5 μm |
| *Agrocybe* | 10-14 μm |
| *Urtica dioica* | 10-12 μm |
| *Periconia* | 16-18 μm |
| *Epicoccum* | 20 μm |
| *Lycopodium clavatum* | 25 μm |
| *Abies* | 125 μm |

-continued

| | |
|---|---|
| *Cucurbitapapo* | 200 μm |
| *Cuburbita* | 250 μm |

Spores, which cause diseases such as farmers' lung are able to do so because they are deposited at a particular location in the lung. By removing the proteinatious and other related materials from the spores to produce the exine coating, we are left with a harmless form able to transport beneficial agents to these same locations in the lung.

A dosage form in accordance with the present invention may be administered by pulmonary inhalation or intra-nasally and may be conveniently delivered by using a dry powder inhaler or a metered dose inhaler aerosol or from a pressurised container, pump, spray or nebuliser with the use of a suitable propellant such as 1,1,2-tetrafluoroethane (HFA 134a) or 1,1,1,2,3,3,3-heptafluoropropane (HFA 227).

Metered dose inhaler compositions may incorporate a surfactant or cosolvent in accordance with conventional practice.

Dosage forms in accordance with the present invention may be administered in the form of a suppository or pessary. Dosage forms, especially incorporating fragments of sporopollenin or spores, may be applied topically in the form of a gel, hydrogel lotion, solution, cream, ointment or dusting powder. The formulations may also be administered dermally or transdermally, for example by use of a skin patch.

Dosage forms of the present invention may be provided for human or veterinary use.

Sporopollenin or other exine coating may be isolated by harsh treatment of spores with a combination of organic solvents and strong acids and alkalis.

BRIEF DESCRIPTION OF THE DRAWINGS

FIGS. 1-14 depict reaction schemes for methods of derivatization/functionalization of sporopollenin in accordance with various embodiments of the present invention.

FIG. 15 is an electron micrograph image of a microtomed cross-section of sporopollenin embedded in acrylic resin.

EXAMPLES

The invention is further described by means of example but not in any limitative sense.

Example 1

Isolation of Sporopollenin from *Lycopodium clavatum*

*Lycopodium clavatum* (250 g, commercially available from Fluka) was suspended in acetone (700 ml) and stirred under reflux for 4 h. The solid residue was filtered, washed with fresh acetone, transferred back to the reaction flask and resuspended in potassium hydroxide solution (850 ml, 6% w/v in water). The mixture was then stirred under refluxed for 6 h. The residue was filtered, washed copiously with hot water, transferred back to the reaction flask, and the hydroxide treatment was repeated. After filtration the solid material was washed with hot water, hot ethanol, and water again. The residue was stirred under reflux in ethanol (750 ml) for 2 h, filtered and washed sequentially with fresh ethanol and dichloromethane. The resulting solid was resuspended in fresh dichloromethane (750 ml), stirred under reflux for 2 h removed by filtration and dried in air for 24 h.

The filtered particles were then suspended in orthophosphoric acid (85%, 800 ml), stirred under gentle reflux for 5 days and filtered. The residue was washed with copious amounts of hot water and sucked dry. The orthophosphoric acid treatment and drying was repeated. The particles were then washed with hot, water, ethanol, and dichloromethane. Finally the solid was stirred under reflux in ethanol (800 ml) for 2 h, filtered and washed with dichloromethane to yield sporopollenin (50 g) that was air-dried and then vacuum dried.

Example 2

Physical Attachment of Thyroxine and Biological Evaluation

Sporopollenin (0.5 g) was compressed under 10 tonnes for 2 minutes. The resulting tablet was added to a solution containing 300 µg thyroxine in 0.3 ml DMSO and 1.5 ml ethanol. The tablet soaked up the solution within a minute and the sample was dried in a vacuum over phosphorus pentoxide at 5° C. until constant weight. The sporopollenin with thyroxine physically attached was administered orally to a volunteer. Within 15 min the thyroxine level in the patient was raised by 1 nano mole/litre of blood. This increase was in parallel with the observation of a significant number of sporopollenin particles/partially degraded particles observed as in Example 18. Thus, assuming that there are 5 litres of blood in the volunteer, 4 µg of thyroxine found after 15 minutes following oral ingestion equates to 0.66% delivery of the drug. This is in keeping with the amount (0.6%) of sporopollenin particles delivered.

Such rapid increase in thyroxine level would not be expected until the elapse of 1-2 h, due to its being primarily absorbed in the jeujenum, which is lower in the gut.

Example 3

Physical Absorption of a Human Recombinant Growth Hormone

Sporopollenin (0.5 g) compressed to form a tablet (16 mm by 3 mm) under 10 tonnes for 2 min. The tablet was added to a solution of a human recombinant growth hormone solid formulation [5.5 mg, which contained the hormone (1 mg) along with a mixture of mannitol, glycine, dibasic sodium phosphate, sodium hydroxide and/or phosphoric acid] in a mixture containing a diluent (0.5 ml; containing glycerol, m-cresol water and sodium hydroxide and/or hydrochloric acid) and ethanol (2.0 ml). The sporopollenin tablet rapidly (15 sec) increased to approximately 4 times its original volume whilst at the same time absorbing all of the solution. The resulting powder was dried under vacuum at 5° C. for 48 h at which time constant weight was achieved.

Example 4

Physical Absorption of a Soluble Insulin Formulation

A solution of soluble insulin (2 cm³ of a formulation which contains 0.18 g insulin, rDNA, zinc chloride, glycerol, meta-cresol, sodium hydroxide, hydrochloric acid and water) and ethanol (1 ml) was added to sporopollenin (1 g) which had been compressed to form a tablet under 10 tonnes for 2 min. The solution was absorbed in 20 seconds at the same time as the sporopollenin tablet increased to approximately 4 times its original volume. The resulting powder was dried under vacuum at 5° C. for 48 h at which time constant weight was achieved.

Example 5

Physical Absorption of Sunflower Oil

Sporopollenin (0.5 g) tablets were prepared by compressing in a 16 mm die at a pressure of 10 tonnes for 2 min. The tablets were added to a mixture of sunflower oil (1 ml) in an absorption aiding liquid (1 ml) at room temperature (Table 1). The resulting powder was dried in a dessicator over $P_2O_5$ in oven at 50° C. until constant weight.

Where no solvent was used the tablet remained virtually unchanged for more than 3 hours.

TABLE 1

| Absorption aiding liquid | Time for complete absorption |
|---|---|
| ethanol | 20 sec |
| diethyl ether | 1 min 5 sec |
| petroleum ether | 3 h |
| dichloromethane | 35 sec |
| hexane | 3 h |
| ethyl acetate | 50 sec |
| acetonitrile | 20 sec |
| toluene | 2 min 15 sec |

The physical attachment involving ethanol and sunflower oil was repeated at 40° C., which reduced the time taken to fully absorb the sample; absorption was complete after 12 seconds. The time for complete absorption is strongly dependant the absorption aiding liquid used and the temperature.

Example 6

Physical Absorption of Glycine

A sporopollenin tablet (0.5 g) was added to 1M glycine solution (0.5 ml) diluted with ethanol (0.5 ml). The solution was rapidly absorbed and the resulting powder dried in under vacuum over phosphorus pentoxide to constant weight. The loading was found to be 1.9 mmol/g of sporopollenin. This experiment was repeated without compressing the sporopollenin. The loading was found to be 0.38 mmol/g of sporopollenin. This shows that there is a significantly greater absorbance of glycine if the sporopollenin is compressed.

The sporopollenin was found to retain 15% of the water-soluble glycine following vigorous stirring in water for 30 min. The same sample was coated with starch and was found to retain 35% of glycine following vigorous stirring for 30 min.

Example 7

Physical Absorption of Copper Sulphate

A sporopollenin tablet (0.5 g) was added to 1M copper sulphate solution (0.5 ml) diluted with ethanol (0.5 ml). The solution was rapidly absorbed and the resulting powder dried in under vacuum over phosphorus pentoxide to constant weight. The loading was found to be 2.5 mmol/g of sporopollenin. The attachment of copper sulphate was shown by SEM-X-ray to be evenly absorbed throughout the sporopollenin shell.

The sporopollenin was found to retain 75% of copper sulphate following stirring for 30 min in water.

Example 8

Physical Absorption of LR White Resin®

Figure 15:
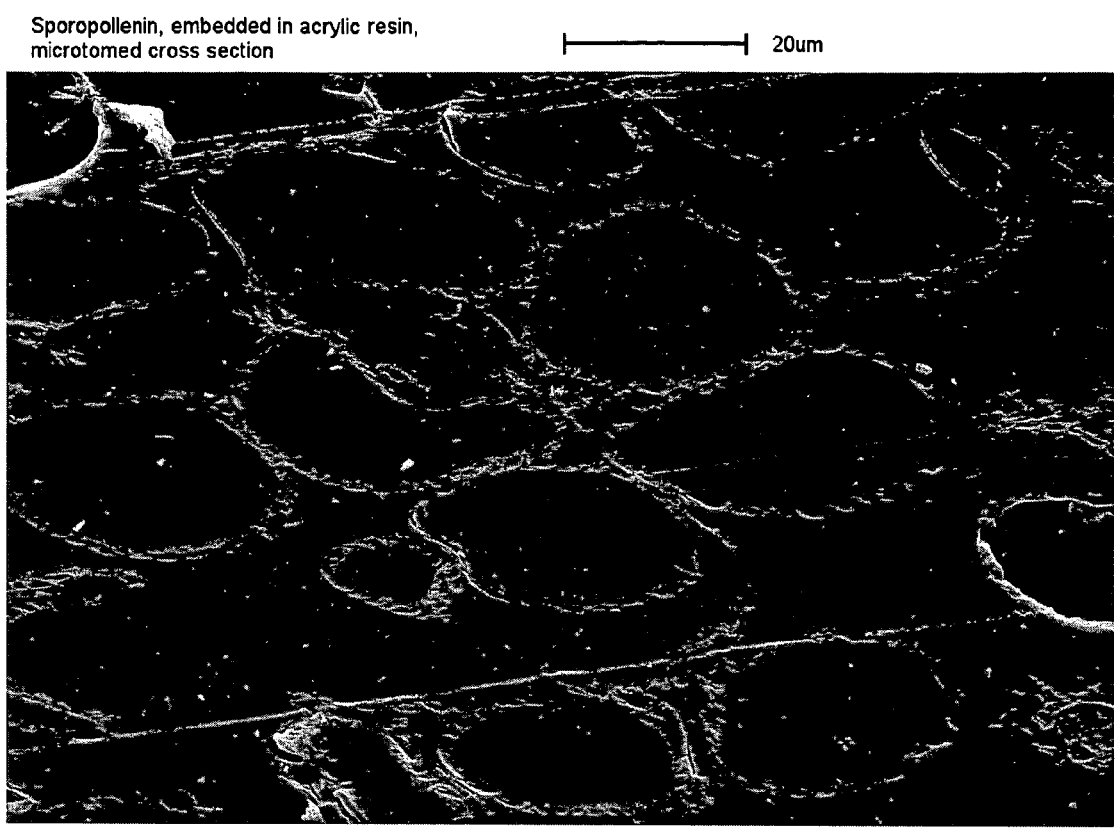

A sporopollenin tablet (0.1 g) was added to 50% ethanolic solution of LR White Resin® (2 ml: 80% polyhydroxy substituted bisphenol A dimethacrylate resin, 19.6% C12 methacrylate ester, 0.9% dimethyl para toluidine). The mixture was gently agitated for 2 h. The resulting particles were separated by centrifugation and further treated with LR White Resin® (2 ml) for a further 12 h. The mixture was then placed in a gelatine capsule and heated at 60° C. for 8 h. The resulting polymer completely filled the inside of the sporopollenin particles and the cavities within the walls as viewed by SEM microscopy (FIG. 15)

Example 9

Derivatisation of Sporopollenin (FIG. 1)

Sporopollenin isolated from *Lycopodium clavatum* may be halogenated at a level of ca. 5 mmol/g by direct bromination (F. Zetsche and K. Huggler, *Liebigs Ann. Chem.*, 1928, 461, 89). It may be chloromethylated by reaction with chlorodimethyl ether and stannic chloride to give a loading of about 1 mmol/g of chlorine (G. Mackenzie and G. Shaw, *Int. J Peptide Protein Res.*, 1980, 15, 298-300). The chloromethyl group was used to synthesise a simple tripeptide using conventional Merrifield methodology. Alternatively, sporopollenin may be aminated with 1,3-diaminopropane to give a loading of 1.6 mmol/g of base R Adamson, S. Gregson and G. Shaw, *Int. J. Peptide Protein Res.*, 1983, 22, 560-564). The 1,3-diaminopropane sporopollenin may be reacted with either chloroacetic anhydride or chloroacetyl chloride followed by treatment with the sodium salt of a 4-hydroxybenzyl alcohol linker. The subsequent benzyl terminating spacer may be used to synthesise a tetrapeptide using conventional methodology. Ion exchange resin type materials have been generated from the diaminoethane derivative of sporopollenin and the acid obtained from the reaction of this material with ethyl bromoacetate/base hydrolysis (loading of 1.4 mmol/g). An acidic product may be obtained by reaction of sporopollenin with chlorosulphonic acid (loading of 1.6 mmol/g) (G. Shaw, M. Sykes, R. W. Humble, G. Mackenzie, D. Marsdan, E. Phelivan, *Reactive Polymers*, 1988, 9, 211-217).

Sporopollenin has the advantage over many commercial polymers in that it is physically and chemically robust but at the same time can be relatively easily derivatised. The most common anchoring groups in commercial polymers which are used as bioconjugates are $BNH_2$, —OH, SH and $CO_2H$. Sporopollenin has the advantage that such anchoring groups can be readily introduced onto its surface to create a covalent linkage with a drug either directly or through a spacer or linker group which forms a short chain between the anchoring group and the drug. We have improved upon the linkers and anchoring groups on sporopollenin over those disclosed in the literature and which are summarised in the previous section. The new linkers/anchoring groups identified below are advantageous over those presented in the literature in terms of convenience of attachment, improved loadings, stability of attachment and minimising toxic by-products in the application of such derivatised sporopollenins as drug delivery materials. It must be noted that sporopollenin particles from one source may be almost identical in their morphology and chemistry. Such consistency may not be found with artificial polymers used on a pharmaceutical scale.

According to a fourth aspect of the present invention there is provided a primary amine functionalised sporopollenin.

Several commercial polymers used for drug delivery such as poly(L-lysine), poly(L-aspartic acid) possess a primary amine group for the attachment of a drug due to its potent nucleophilicity which permits it to be a particularly versatile linker/anchor functional group for a wide variety of drug vector applications. Normally, the amine group is coupled to carboxyl-containing drugs with the use of carbodiimide reagents. The primary amine can also be reacted with disuccinimidylcarbonate and triethylamine to give an isourea (Bioconjugate Techniques by Greg T Hermanson, 1996, Academic Press Inc and Bioconjugation in pharmaceutical chemistry by Il Farmaco, 1999, 54, 497-526 and references therein) which can attach amine carrying drugs such as insulin.

A preferred aspect of the present invention provides a novel approach to derivatising sporopollenin with a primary amine functional group with minimal chemistry and avoiding the use of non-toxic spacer groups such as diamines as previously used. The approach involves treating sporopollenin with aqueous ammonia (0.880) at room temperature, to give an aminated form of sporopollenin, which is subsequently reduced with $LiAlH_4$ to give a primary amino (—$NH_2$) form of the polymer. A loading of ca. 1 mmol/g may be obtained.

Example 10

Figure 2:
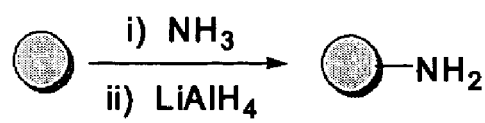

Preparation of Primary Amine Functionalised Sporopollenin (FIG. 2)

Sporopollenin (2 g) was stirred in 0.880 ammonia at room temperature for 4 days. The sporopollenin was collected by filtration and washed with water (10×100 $cm^3$), EtOH (2×30 $cm^3$) and DCM (2×30 $cm^3$). The sporopollenin was then dried in vacuo to a constant weight. $LiAlH_4$ (3.6 g) was stirred under $N_2$ in dioxane (100 $cm^3$). The aminated sporopollenin (2. g) was added and refluxed under $N_2$ for 4 days. The mixture was cooled.

Ethyl acetate (100 $cm^3$) was added with caution and cooling. Any large insoluble lumps were broken up with a glass rod. Water (100 $cm^3$) was added slowly followed by 2M sulphuric acid (200 $cm^3$). The primary amino sporopollenin was then washed with water (2×250 $cm^3$), EtOH (2×250 $cm^3$), DCM (2×250 $cm^3$) and dried to a constant weight (1.8 g) under vacuum.

According to a fifth aspect of the present invention there is provided a polyamino functionalised exine coating. A dosage form comprising a polyamino functionalised sporopollenin chemically bound to an effective quantity of an active substance is also provided.

Some polyamino compounds such as spermine and spermidine occur naturally in the body. These are non-toxic hence have applications as spacer groups. In a preferred embodiment a polyamino compound may be caused to react with sporopollenin by heating or refluxing in an inert solvent to form a covalent bond.

An advantage of using polyamines over diamines and primary amines is the availability of the additional nucleophilic amino groups for drug attachment to provide such derivatised sporopollenins and similar exine coatings with an increased loading capacity of drugs. Aromatic polyamines such as 1,3, 5-phenylenediamine and related heterocycles such as melamine may be used in a similar manner. Aromatic amines can be readily activated as isocyanates or isothiocyanates using phosgene or thiophosgene respectively and with hydroxyl-carrying drugs such as nucleosides (e.g. D4T, acyclovir and AZT). Example 11 discloses the protocol by which, such an anchor or spacer group may be attached.

Example 11

Figure 3:
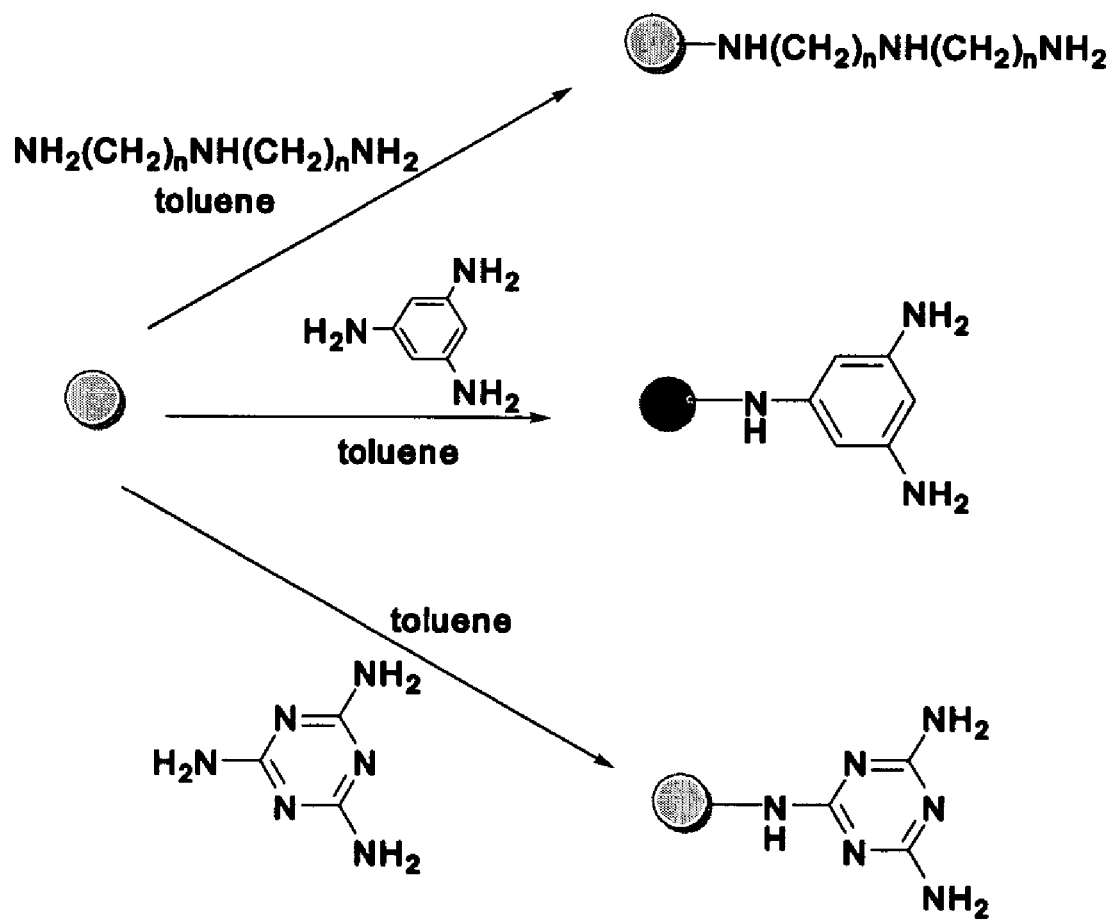

Preparation of Polyamine Functionalised Sporonollenin (FIG. 3)

Spermidine (0.7 mmol), 1,3,5-phenylenediamine (0.7 mmol) and melamine, were each refluxed with sporopollenin (0.1 g) in a variety of solvents such as toluene (10 ml), dimethyl sulphoxide (DMSO) and dimethyl formamide (DMF) for 24 hours to give loadings of 1.6, 0.95 and 0.54 mmol/g respectively after filtration and washing with toluene ($2\times10$ cm$^3$), 2M HCl ($2\times10$ cm$^3$), water ($3\times10$ cm$^3$), EtOH ($2\times10$ cm$^3$) and DCM ($2\times10$ cm$^3$) and drying under vacuum to a constant weight.

According to a sixth aspect of the present invention there is provided a carboxylic acid functionalised exine coating. A dosage form comprising of carboxylic acid functionalised exine coating chemically bound to an effective quantity of an active substance is also provided.

A common method of forming drug-polymer conjugates involves activation of a carboxylate function via the N-hydroxysuccinimidyl esters using N-hydroxysuccinimide and a carbodiimide. Such activated esters can couple efficiently with primary amine carrying drugs such as peptides and hydroxyl containing drugs such as nucleosides. A number of commercially available carbodiimides are soluble in either aqueous or organic solvents. The attachment of carboxylic acid linkers to sporopollenin has been disclosed (G. Shaw, M. Sykes, R. W. Humble, G. Mackenzie, D. Marsdan, E. Phelivan, *Reactive Polymers*, 1988, 9, 211-217). This work involved the reaction of 1,3-diaminopropane derivatised sporopollenin with ethyl bromoacetate followed by saponification. Improved loadings can be achieved by, for example, reacting the aforementioned polyamino derivatised sporopollenins with, for example, succinic anhydride or ethyl bromoacetate, and subsequent saponification. An alternative means of introducing a carboxylic acid function is the attachment of an amino acid or short peptide chain such as either Gly-Phe-Ala-Leu or Gly-Phe-Leu-Gly. Attachment of an amino acid as a linker onto an exine coating is attractive since it is achieved easily by either heating or refluxing an unprotected amino acid or ethyl or other alkyl ester of an amino acid with an exine coating in an appropriate solvent. A further advantage of such linkers is their non-toxicity. Example 12 discloses a protocol for the attachment of an underivatised amino acid to sporopollenin.

Example 12

Figure 4:
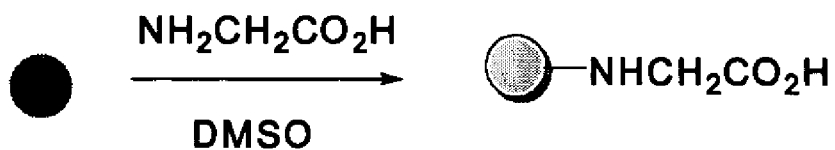

Preparation of Amino Acid Functionalised Sporopollenin as a Means to Attach a Carboxylic Acid Function (FIG. 4)

A mixture of glycine (0.1 g) and sporopollenin (0.1 g) was refluxed in DMSO for 24 hours. The sporopollenin were collected by filtration and washed with toluene ($2\times10$ cm$^3$), EtOH ($2\times10$ cm$^3$), 2M HCl ($2\times10$ cm$^3$), water ($3\times10$ cm$^3$), EtOH ($2\times10$ cm$^3$) and DCM ($2\times10$ cm$^3$) to give a loading of 3.6 mmol/g.

Example 13 illustrates a protocol for the attachment of an amino acid ester to sporopollenin and subsequent provision of an available carboxyl function.

Example 13

Figure 5:
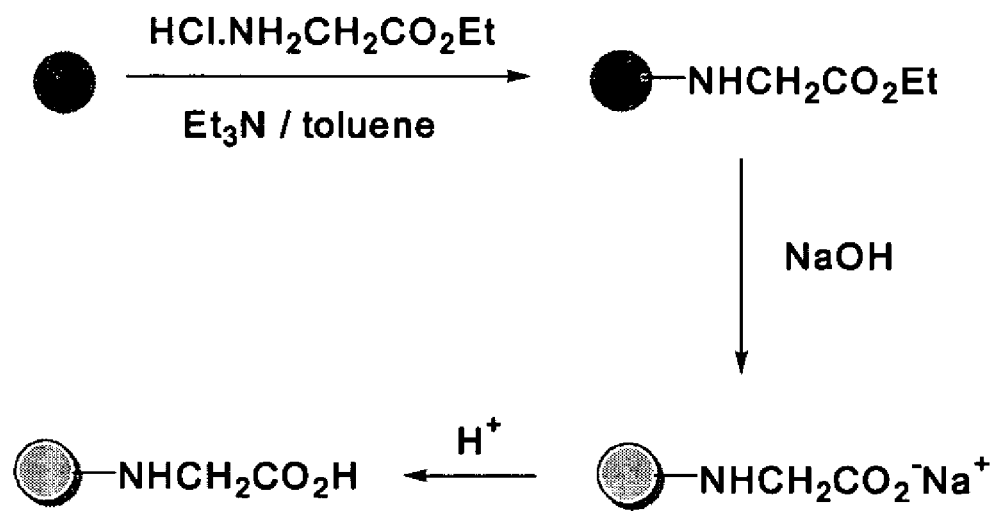

Preparation of an Amino Acid Ester Functionalised Sporopollenin as a Means to Attach a Carboxylic Acid Function (FIG. 5)

Glycine ethyl ester hydrochloride (0.1 g) was stirred in toluene (20 cm$^3$) and triethylamine (2 ml). Sporopollenin (0.1 g) was added and the mixture was refluxed for 24 hours with stirring. The cooled derivatised spores were collected by filtration and washed with toluene ($2\times10$ cm$^3$), EtOH ($2\times10$ cm$^3$), 2M HCl ($2\times10$ cm$^3$), water ($3\times10$ cm$^3$), EtOH ($2\times10$ cm$^3$) and DCM ($2\times10$ cm$^3$). The sporopollenin was then dried under vacuum and showed a loading of 1.7 mmol/g. Hydrolysis of the ethyl ester function to the sodium salt of the corresponding carboxylic acid was achieved by refluxing with 2M NaOH (20 ml) for 2 hours. Neutralisation with 2M HCl (40 ml) at room temperature followed by washing with water and drying under vacuum gave the required acid (loading 2.8 mmol/g).

The above procedure was also followed for the ethyl ester hydrochlorides of such as, β-alanine, L-lysine, α-L-alanine, aspartic acid glutamic acid and aminomalonate with loadings in the range of 1.0 to 2.5 mmol/g. The advantage of attaching aminomalonate, aspartic acid or glutamic acid is that they make available two carboxylate functions to permit the additional loading capacity of a drug.

According to a seventh aspect of the present invention there is provided a polyhydroxyl functionalised exine coating. A dosage form comprising a polyhydroxyl functionalised exine coating chemically bound to an effective quantity of an active substance is also provided.

Polyhydoxyl linkers obtained largely from carbohydrates have the advantages of ease of attachment, non-toxicity and high loadings resulting from the availability of a number of hydroxyl groups depending on the nature of the sugar attached to the exine coating. The availability of a large number of hydroxyl groups on exine coating has the advantage of permitting attachment of a large variety of drugs. The stability along with the chemical and morphological consistency of polyhydroxyl derivatised exine coatings have advantages over polysaccharide drug vectors such as starch, cellulose and non-spore derived chitosan. The latter polymers are not found with the same chemical and/or morphological consistencies, or the same resistance to acids and alkalis and hygroscopicity as sporopollenin or its equivalent exine coating.

Hydroxyl groups on such conjugate materials can be transformed into many activated species that are suitable for synthesising drug-polymer conjugates. For example the OH groups can be activated as mesylates and tosylates along with succinimido- and imidazolyl-carbonates and p-nitrophenylformates. All of these react readily with primary amine containing drugs such as peptides. Hydroxyl groups may also be oxidised to aldehydes or ketones.

Primary amine containing drugs may be attached by reductive amination. The OH groups on the polymer can also be activated with CNBr to form cyanate esters, which react with amine containing drugs. Thus a drug-polymer conjugate derived from a carbohydrate may be coupled to an exine coating to give a conjugate with a large number of reactive hydroxyl groups and which is chemically and morphologically consistent. Example 14 illustrates a method by which a polyhydroxyl linker may be attached to sporopollenin.

Example 14

Figure 6:
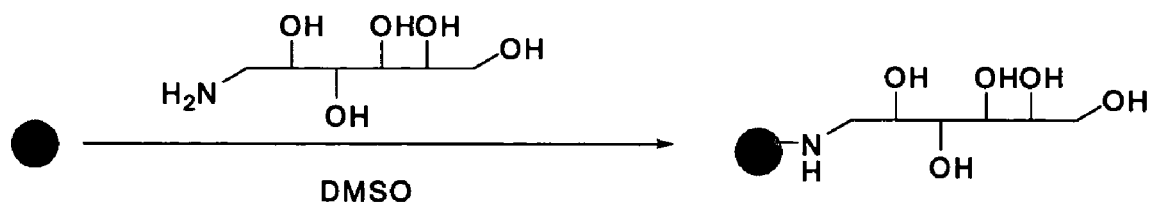

Preparation of Polyhydroxyl Functionalised Sporopollenin (FIG. 6)

Sorbitolamine (0.13 g, 0.69 mmol) was stirred in DMSO (10 cm$^3$). Sporopollenin (0.1 g, 0.23 mmol) was added and the mixture refluxed for 24 hours. The cooled spores were collected by filtration and washed with DMSO (2×10 cm$^3$), water (100 cm$^3$), EtOH (2×10 cm$^3$) and DCM (2×10 cm$^3$). The sporopollenin was dried under vacuum to a constant weight to give a loading of 1.7 mmol/g.

Example 15

Figure 7:
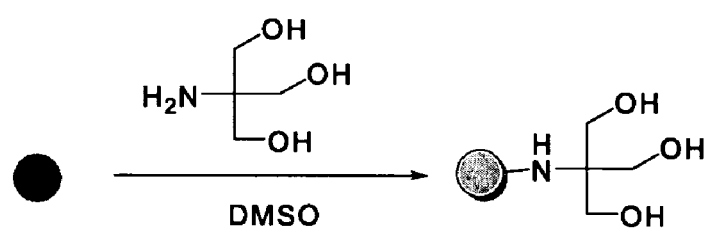

Preparation of tris(hydroxymethyl)methylamine-sporopollenin (FIG. 7)

A similar procedure to Example 14 using tris(hydroxymethyl)methylamine gave a loading of 0.83 mmol/g.

Example 16

Preparation of Fluorescein and Thyroxine Covalently Attached Sporopollenin

Fluorescein (0.5 g) and thyroxine (0.5 g) were each refluxed with sporopollenin (0.1 g) in DMSO (20 ml). The cooled sporopollenin was collected by filtration and washed with water (100 cm$^3$), EtOH (2×10 cm$^3$) and DCM (2×10 cm$^3$). The sporopollenin was dried under vacuum to a constant weight to give loadings of 1.0 and 0.37 mmol/g respectively.

This type of attachment is extremely efficient if the drug or other active substance is sufficiently stable to withstand the refluxing step. Such a means of direct attachment has distinct advantages over use of many commercial polymers, which are not as chemically stable as sporopollenin.

Less stable drugs such as insulin can be attached to aminosporopollenin, via such as a succinylamido spacer and using DCC and HOBt as coupling agents. An advantage of sporopollenin in such couplings over commercial polymers is its chemical consistency such that the loadings expected for the coupling of drugs to each batch of sporopollenin should be highly consistent. A protocol for the attachment of drugs such as insulin as illustrated in the following procedure:

Example 17

Preparation of Insulin-Coupled Sporopollenin

Succinic anhydride (0.57 g, 5.7 mmol) dissolved in dry dimethylformamide (DMF, 15 ml) was added to a suspension of aminosporopollenin (1 g) in dry DMF (30 ml). The reaction mixture was stirred overnight at room temperature under nitrogen. The product was isolated by filtration, washed with acetone and dried under vacuum for 48 h in the presence of P$_2$O$_5$. DCC (3.80 g, 18.4 mmol) and HOBt (2.27 g, 1.84 mmol) in dry DMF were added successively to a suspension of the succinylamidosporopollenin in dry DMF (20 ml). The mixture was stirred under nitrogen for 3 h at room temperature and freeze-dried insulin (0.2 g) was added as a solution in dry DMF (20 ml). The mixture was stirred for 48 h at room temperature. The reaction was stopped by the addition of water (10 ml) at 0° C. The mixture was gently stirred for 2 h at room temperature, filtered and washed with acetone and ether to give the insulin-succinylamido sporopollenin with a loading of 0.03 mmol/g.

The above example illustrates how proteins and enzymes may be attached to sporopollenin and similar exine coatings. Oligonucleotides, such as antisense oligonucleotides may be attached by similar chemistry to permit the delivery of such drugs by an oral route. Previously such compounds were delivered by injection often as PEG-3'-oligonucleotide or PEG-5'-oligonucleotide conjugates. Similar synthetic coupling reactions to those used to synthesise PEG-3'-oligonucleotide or PEG-5'-oligonucleotide conjugates may be employed using the hydroxylated anchored sporopollenins previously described.

The application of sporopollenin-drug type conjugates of drugs such as taxanes and cyclosporins, which have poor water solubility has particular benefits. Such drugs can be attached to sporopollenin under a variety of conditions, for example, using coupling agents in highly effective solvents such as DMSO or buffered aqueous solvents. When the sporopollenin-drug type conjugates arrive in the blood stream following oral administration the drugs may be released in a highly dispersed manner and hence may be better solvated by the blood serum. Thus sporopollenin and similar exine coatings may be an alternative to the use of polyethylene glycols (PEGs), which are often used to derivatise drugs with poor solubility in aqueous systems. Such conjugates may be advantageous in that they could be taken orally as opposed to injection as is the case with PEG-drug conjugates.

Example 18

Biological Evaluation

Two subjects consumed sporopollenin (1 g; 25 µm; derived from *Lycopodium clavatum*) in the clinic and blood samples were taken in 30 minute intervals.

The blood samples (20) were centrifuged at 3000 rpm for 8 min. The serum was then removed and the residual material transferred, by several rinses of water (10 ml total), to larger tubes. The samples were then mixed thoroughly and centrifuged once more. The supernatants were removed and the pellet and residual liquid (0.5 ml) resuspended in 0.5 ml glycerol.

Aliquots of approx 0.1 ml were then taken and examined by light microscopy. The entire area under the cover slip was examined.

The sporopollenin particle counts were carried out as follows. The total number of particles were calculated by counting intact particles and groups of fragments which were clumped together. These fragments were assumed to have been derived from one sporopollenin particle but may have contained components of several.

The results of microscopy examination were as follows:
Samples from first human subject (following foods)
1) before administration of sporopollenin:
   No particles were found
2a) 30 min after administration:
   80 particles of which 12 were intact and the remainder were clusters of 10-20 fragments.
2b) 30 min after administration:
   45 particles were found of which 7 were intact, the rest fragments.

3a) 60 min after administration:
   2 intact particles and 27 groups of tiny fragments were found.
3b) 60 min after administration:
   20 groups of tiny fragments and no intact particles were found.
4) 90 min after administration:
   1 intact particle and 12 groups of very small fragments were observed
5) 120 min after administration:
   A few small fragments were observed
Samples from second human subject (fasted):
1) before administration of sporopollenin:
   No particles were found
2a) 30 min after administration:
   3 intact particles and 48 very small fragments were found
2b) 30 min after administration:
   4 intact particles and 35 fragment areas were found
3a) 60 min after administration:
   1 intact particles and 17 areas of extremely small fragments were observed
3b) 60 min after administration:
   2 particles and 15 areas of fragments were seen.
4) 90 min after administration:
   No particles or fragments were found The minimum proportion of sporopollenin entering into the blood stream from 1 g was estimated to be 0.60%

Estimates of Amount of Drug-Sporopollenin Conjugates Required for Therapeutic Efficacy:

Assuming an average loading of 1 mmol g$^{-1}$, the amount of a drug entering into the blood stream from 1 g of sporopollenin would be 0.006 mmol For 1 g of sporopollenin with insulin (M. W. 6000) attached, either physically or covalently, at 0.03 mmol/g would give 11 mg (0.018 mm) of available insulin into the blood stream that is of the order of 30 IU. As the normal person produces 24 u insulin per day and the average diabetic is on 60 u per day then a maximum of 2 g of sporopollenin would be equivalent 1 day's supply of insulin assuming subcutaneous dosing would be equivalent efficacy as the oral route.

For thyroxine (M. Wt 776.9) attached to 1 g of sporopollenin at a loading of 0.37 mmol/g would give 1.7 mg of available thyroxine, [approximately 17 doses (average dose 100 µg)]. The physical attachment of thyroxine to sporopollenin at a loading of 600 µg/g would be expected to deliver 3.6 µg into the blood stream. This value was supported by the analysis of thyroxine found in the blood of a volunteer at 4 µg/5 litres after 15 minutes following oral ingestion (i.e 0.66% delivered which is in keeping with the amount of sporopollenin particles delivered).

Sporopollenin or other similar exine coatings can be multiderivatised. In this way sporopollenin can be used as to deliver more than one drug in a single dose. In addition, a drug together with an activating agent may be both bound to the same sporopollenin particle. Furthermore such multifunctionality may be used to introduce a functional group such as a fatty acid chain, to form a type of lipoconjugate, or a polyethylene glycol (PEG) to form a PEG-lipid type conjugate to protect an attached drug by steric hinderance and possible enable slower release of the drug, once the attached particles have arrived in the bloodstream. For example, the residual double bonds and carboxylic acid groups of sporopollenin can be derivatised separately. Thus the double bonds are firstly reacted with bromine to form bromosporopollenin, which is reacted with sodium azide to form the novel azidosporopollenin which is reduced with lithium aluminium hydride to form a primary aminosporopollenin. The primary amine is reacted with a drug such as the antiviral drug AZT monophosphate in buffer solution and EDC as coupling agent to give AZT monophosphorylsporopollenin. The remaining carboxylic acid groups on sporopollenin are then condensed with hexadecylamine using DDC. The hexadecyl moiety could then act to provide additional protection of the attached drug during its short time in the stomach. An example of a methodology for this type of attachment is as follows (FIG. 8).

According to an eighth aspect of the present invention there is provided a halogeno functionalised exine coating. A dosage form comprising a halogeno functionalised exine coating chemically bound to an effective quantity of an active substance is also provided.

Example 19

Introduction of a Primary Amine by Bromination, Azidation and Reduction

Sporopollenin (1 g) was stirred for 24 h in 30% bromine in acetic acid (10 $cm^3$). The sporopollenin was recovered by filtration and washed with methanol (10×5 $cm^3$) and ether (5 $cm^3$) and dried under vacuo to give bromosporopollenin (A, FIG. 8). A solution of sodium azide (1.25 g, 19.2 mmol) in DMSO (30 $cm^3$) was added and the mixture was heated at 60° C. for 48 h. The resulting azidosporopollenin (B, FIG. 8) was collected by filtration, washed, dried (1.8 mmol/g of $N_3$) and refluxed for 1 h with a mixture of lithium aluminium hydride (0.2 g) in THF (15 $cm^3$). The mixture was cooled to room temperature, washed and dried to give the aminosporopollenin (C, FIG. 8) (1.4 mmol/g of $NH_2$).

Example 20

Attachment of AZT Monophosphate

AZT monophosphate (2.1 mmol) was added to a stirred suspension of aminosporopollenin (0.3 g; 1.4 mmol/g of $NH_2$) in 0.1 M MES, pH 4.7-6.0 buffer solution (15 $cm^3$). EDC (2.1 mmol) was added and the mixture stirred for 18 h at room temperature. The particles were filtered, washed with water and dried under vacuum to give to give AZT monophosphoramidatesporopollenin (D, FIG. 8)(1 mmol/g).

Example 21

Attachment of Hexadecylamine

A mixture of AZT monophosphorylsporopollenin (0.3 g; 1 mmol/g) and DCC (2.1 mmol) in DMSO (10 $cm^3$) was stirred for 18 h. The resulting hexadecylamino(1 mmol/g)/AZT monophosphoramidate (1 mmol/g) sporopollenin (E, FIG. 8) was removed by filtration and dried under vacuum.

Sporopollenin possess residual hydroxyl groups at a loading of ca. 1 mmol/g, as determined by Fmoc analysis (Route A in FIG. 9). These functional groups can be used to attach drugs directly or via spacer groups[1].

Example 22

Alkylation of OH Groups

A suspension of sporopollenin (1 g; 1 mmol/g) and chloroacetic acid (6 mmol) in 6 M NaOH (50 $cm^3$) was stirred for 18 h to give after washing and drying sporopollenin-acetic acid with a loading of 0.8 mmol/g (Route B in FIG. 9).

Example 23

Figure 9:
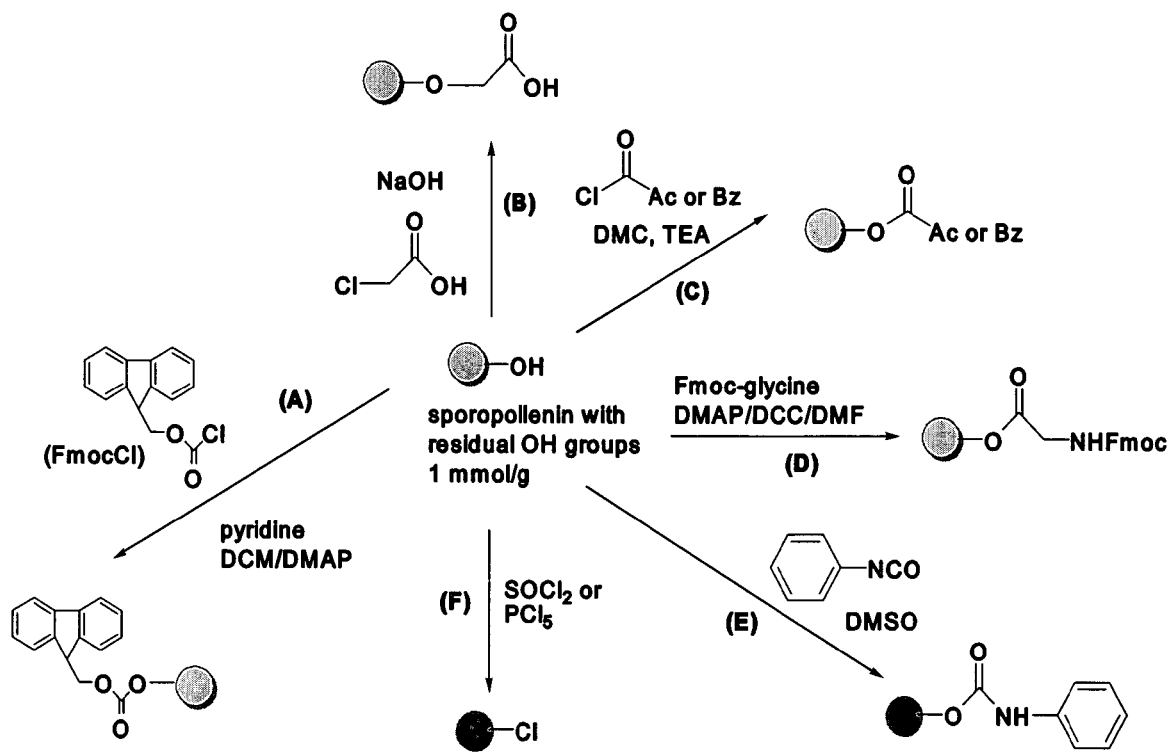

Acylation of OH Groups (i) Using Anhydrides and Acid Chlorides:

The residual hydroxyls can be readily acetylated[2,3,4] by reagents such as acetyl chloride or acetic anhydride and benzoylated by benzoyl chloride under standard conditions to give acylated sporopollenins (Route C in FIG. 9). Benzoyl chloride (5 mmol) was added to a stirred suspension of sporopollenin (0.1 g; 1 mmol/g OH) in DCM (10 cm$^3$), DMAP and pyridine (3 mmol) cooled in an ice bath. The benzoylated sporopollenin (0.6 mmol/g benzoylated) was filtered, washed and dried.

(ii) Using an N-protected Amino Acid and Coupling Agent:

Direct acylation of the hydroxyl groups with N-protected amino acids such as Fmoc glycine (Route D in FIG. 8) and a coupling agent such as DCC catalysed by DMAP has not been published. Thus an example of such a methodology is as follows: A solution of DCC (0.5 mmol) and Fmoc glycine (1 mmol) in DCM (20 cm$^3$) and DMF (1 cm$^3$) were stirred for 20 min. The DCM was removed by evaporation and a solution of the residue dissolved in DMF (10 cm$^3$) was added to a suspension of sporopollenin (0.1 mmol/g) in DMF (10 cm$^3$). A solution of DMAP (0.1 mmol) in DMF (2 cm$^3$) was added and the resultant mixture was stirred for 24 h. The Fmocglycyl sporopollenin was filtered, washed with DMF, DCM and MeOH and dried (0.41 mmol/g Fmoc glycine).

A similar method of attachment may be employed to attach peptide and protein drugs.

(iii) Carbamation of Hydroxyl Groups:

The residual hydroxyl groups can react with isocyanates (Route E in FIG. 3). This method may be used to form heterobifunctional linkers for coupling of hydroxyl groups using p-maleimidophenyl isocyanate. Sporopollenin has been derivatised with phenyl isocyanate as follows: A suspension of sporopollenin (1 g; 1 mmol/g) and phenyl isocyanate was stirred and heated at 80° C. for 18 h to give the sporopollenincarbamate (0.9 mmol/g) which was filtered and washed with DMSO and methanol and dried.

Figure 8:
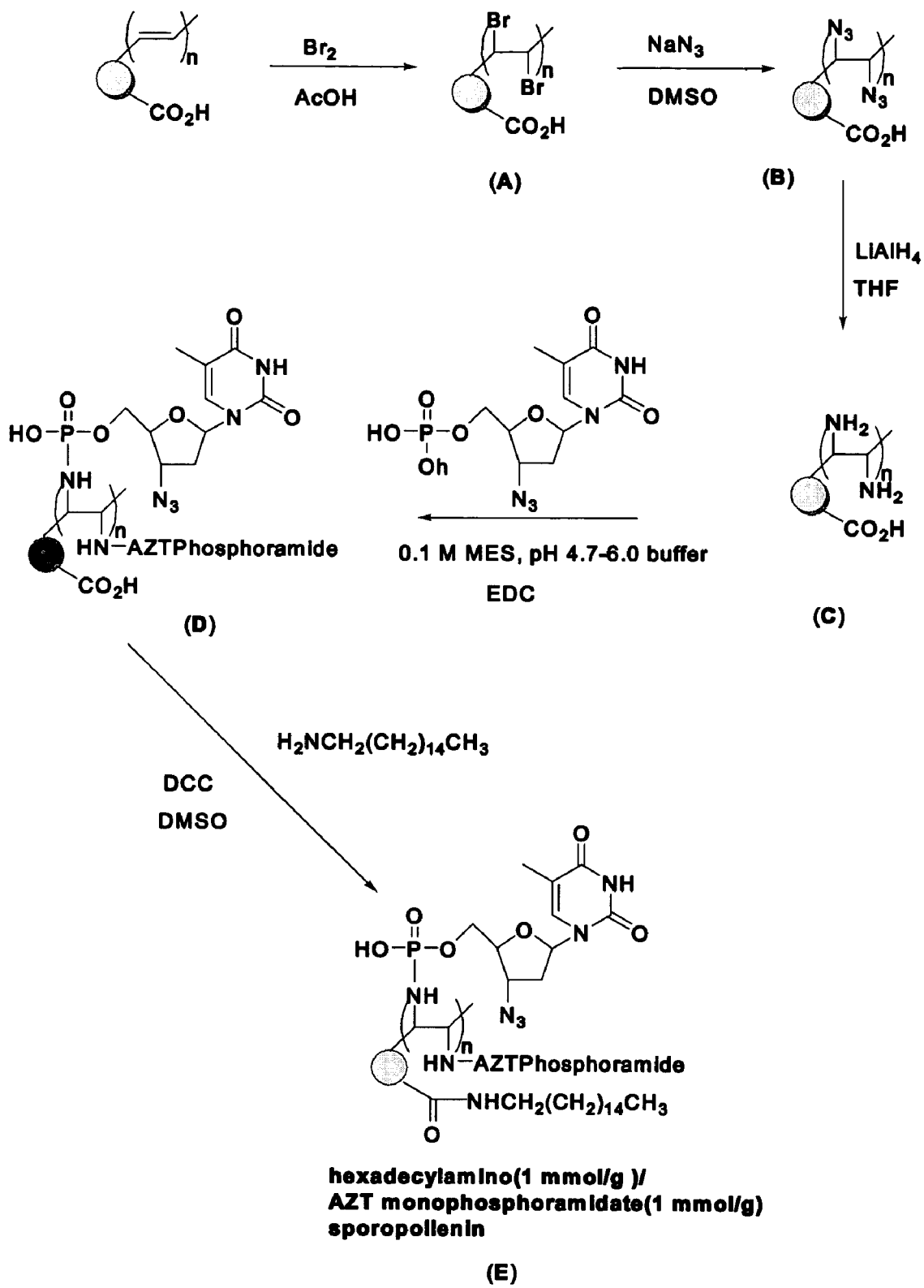

(iv) Halogenation of Hydroxyl Groups:

The residual hydroxyl groups of sporopollenin can be readily halogenated with $SOCl_2$, $POCl_3$ or $PCl_5$ (Route F in FIG. 8). Such halogenated forms of sporopollenin can be used to further derivatise the polymer by a linker followed by a drug. Halogenation of the hydroxyl groups is illustrated by the following: Anhydrous potassium carbonate (6.37 mmol) and sporopollenin (1 g; 1 mmol/g OH) was added to a solution of $PCl_5$ in DCM at 0° C. The mixture was stirred for 15 min after which the sporopollenin was removed by filtration, washed with DCM and ethanol and dried (1 mmol/g Cl).

REFERENCES

1 S. Kettley, PhD University of Hull, 2001.
2. G. Shaw, The Chemistry of Sporopollenin, in: *Sporopollenin*, J. Brooks, M. Muir, P. Van Gijzel and G. Shaw, (Eds) Academic press, London and New York, 1971, 305-348.
3. F. Zetche, P. Kalt, J. Liechti, E. Ziegler, *J. Prakt. Chem.*, 1937, 148, 267.
4. P. Fawcett, D. Gree, R. Holleyhead and G. Shaw, *Grana*, 1970, 10, 246.
5. M. E. Annunziato, U.S. Patel, M. Ranade and P. S. Palumbo *Bioconjugate Chem.*, 1993, 4, 212.

Several bioconjugates make use of thiol anchor groups (Bioconjugate Techniques Greg T Hermanson, 1996, Academic Press Inc and Bioconjugation in pharmaceutical chemistry, Il Farmaco 1999, 54, 497-526). Sporopollenin can be readily derivatised to introduce a thiol group by, for example, first bromination of the sporopollenins double bonds followed by treatment with either thiourea (FIG. 10) or NaSH.

According to a nineth aspect of the present invention there is provided a thiol functionalised exine coating. A dosage form comprising a thiol functionalised exine coating chemically bound to an effective quantity of an active substance is also provided.

Example 24

Figure 10:
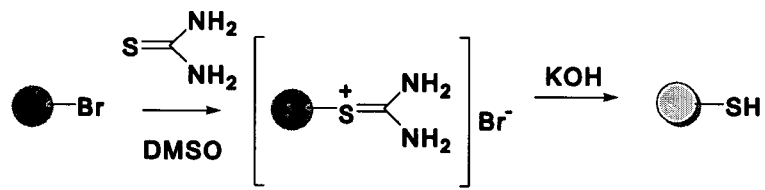

Attachment of a Thiol Group to Sporopollenin (FIG. 10)

A stirred suspension of bromosporopollenin (1 g, 4.5 mmol/g; obtained as previously described by reaction of sporopollenin with bromine in acetic acid) and thiourea (60 mmol) in DMSO (10 cm$^3$) was refluxed for 24 h. The product was collected by filtration and washed with DMSO, water, 2M HCl, water, EtOH and DCM. The particles were stirred in 25% KOH for 6 h under reflux. After cooling the particles were filtered and washed with water, 2M HCl, water and methanol and dried to give the thiolated sporopollenin (5.2 mmol/g).

Example 25

Figure 11:

Attachment of a p-nitrobenzoyloxycarbonyl Group to Sporopellenin (FIG. 11)

Acylation of thiol groups with p-nitrobenzoyloxycarbonyl chloride (FIG. 11): Thiolated sporopollenin (5.2 mmol/g) was stirred under $N_2$ with DCM (25 cm$^3$) containing p-nitrobenzoyloxycarbonyl chloride (30 mmol) and triethylamine (30 mmol) under reflux. The particles were filtered, washed with DCM and methanol and dried to give the p-nitrobenzoylthiooxycarbonylated sporopollenin (2.45 mmol/g).

Figure 12:
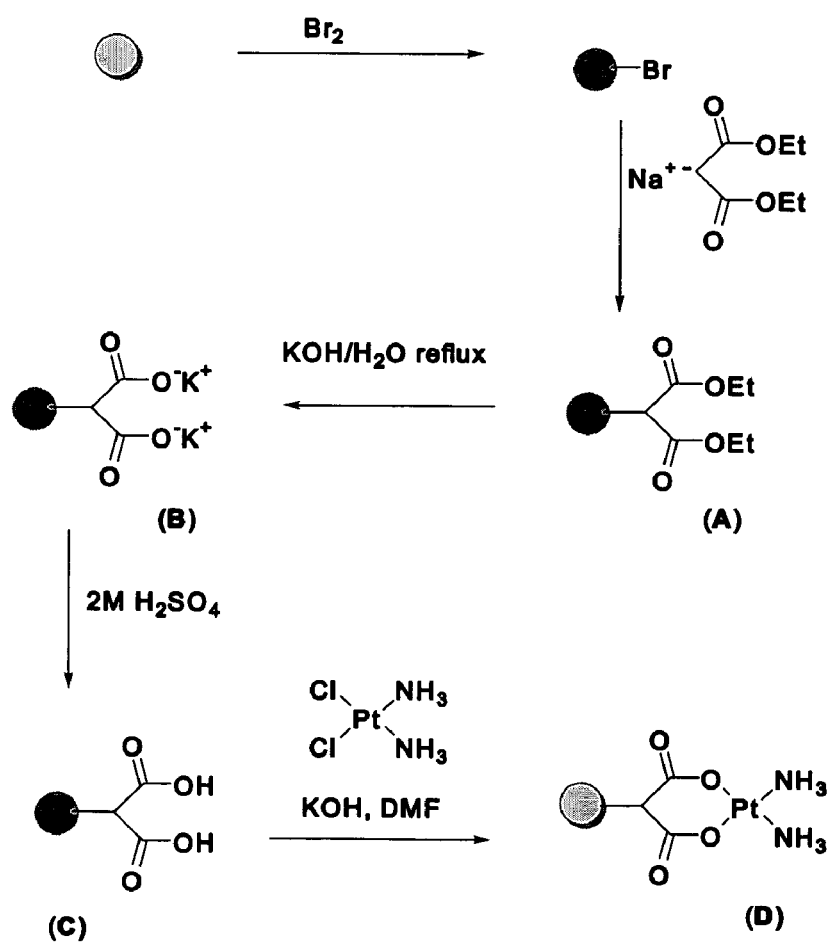

There are many methods, which may be used to effect carbon-carbon attachments to sporopollenin. The structure of this rather complex but physically and chemically stable polymeric substance is not fully known; hence it is difficult to know what reactions might be found to take place at its surface in the future. However, a simple example of carbon-carbon bond formation involves reaction of diethyl malonate with bromosporopollenin in sodium ethoxide solution to generate, after hydrolysis with KOH solution and neutralisation with a mineral acid to give a diacid functionalitality on sporopollenin (Structure C, FIG. 12) and hence increase the loading of $CO_2H$ groups. An example of such methodology is as follows:

According to a tenth aspect of the present invention there is provided a functionalised exine coating via a carbon-carbon bond. A dosage form comprising an exine coating, a carbon-carbon bond, other functional group(s) bound to an effective quantity of an active substance is also provided.

Example 26

Attachment of a Carbon-Carbon Bond Attachment of a Functional Group to Sporopollenin.

Diethyl malonate (25 mmol) was added slowly to a solution of sodium methoxide (30 cm$^3$; 25 mmol Na) at 50° C. The resulting solution was slowly added to a stirred suspension of bromosporopollenin (1 g; 5 mmol/g Br) in ethanol (50 cm$^3$). Following the addition (15 min) the mixture was refluxed for 18 h. The diethyl malonyl sporopollenin (A, FIG. 12) was removed by filtration and washed with ethanol. Potassium hydroxide (15 mmol) was dissolved in water (2 cm$^3$) and added to ethanol (10 cm$^3$). The solution was added to a stirred suspension of diethyl sporopollenin diethyl malonate (A, FIG. 12) in ethanol (40 cm$^3$) and refluxed for 18 h. The particles were removed by filtration and washed with water and ethanol and dried to give the potassium salt (B, FIG. 12). A suspension of B in ice-cold water was acidified with dilute sulphuric acid to give after washing with water and ethanol and drying, the sporopollenin malonic acid (C, FIG. 12) (1 mmol/g).

Figure 13:
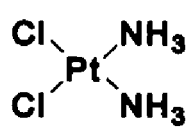
Figure 13:
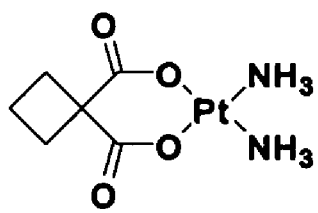
Figure 13:
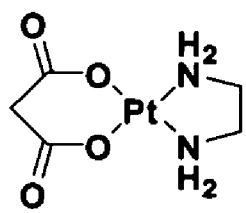
Figure 13:
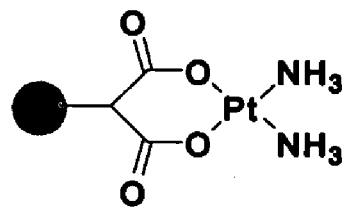

Metals have been attached to spacer groups attached to sporopollenin to produce a filtration material and not in relation to drug delivery {G. Shaw, M. Sykes, R. W. Humble, G. Mackenzie, D. Marsdan, E. Phelivan, *Reactive Polymers*, 9, (1988), 211-217}. However, no drugs possessing a metal complex have been disclosed. The following example discloses a method in which sporopollenin acts as a ligand to platinum (D, in FIG. 12). This is analogous to well known antitumour drugs such as cisplatin, CBDCA and JM-40 (FIG. 13). The method by which the novel derivative (D, in FIG. 12) is synthesised is outlined in FIG. 12 and is detailed as follows:

Example 27

Attachment of Cisplatin to Sporopollenin

A solution of cis-[PtCl$_2$(NH$_3$)$_2$] (1.33 mmol) in DMF (20 cm$^3$) was added to a stirred suspension of sporopollenin malonic acid (C, FIG. 12) in DMF (20 cm$^3$). This was followed by the addition of 0.1 M aqueous KOH (27 cm$^3$) and the resulting mixture was stirred at 60° C. for 48 h. Sporoplatin (D, in FIG. 12 and shown, as named, in FIG. 13) was removed by filtration and washed with water, ethanol and ether (0.9 mmol/g).

A number of gold(I)thiolate complexes show potent activity against rheumatoid arthritis. The most successful of such drugs include Myochrysine, Solganal, Allochrysine and, more recently, the orally administered Ridaura. (R. Bau, *J. Am. Chem. Soc.* 1998, 120, 9380). Ridaura is a thiosugar/phosphine complex of gold and, as with many sugars, suffers degradation in the digestive system. A related sporopollenin/phosphine complex of gold may be more stable in the gut and can more rapidly deliver gold(I)thiolate into the bloodstream for treatment of rheumatoid arthritis. Platinum, ruthenium, gadolinium and technetium complexes may also be employed.

Example 28

Figure 14:
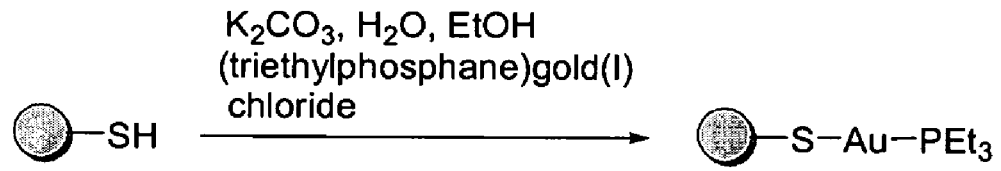

Gold(I)thiolate Complex of Sporopollenin (FIG. 14)

Potassium carbonate (1 mmol) in ethanol-water (1:4; 50 cm$^3$) was added to a suspension of thiolated sporopollenin (1 g; 1 mmol/g) and stirred for 5 h at room temperature and cooled to 0° C. A solution of (triethylphosphane)gold(I) chloride (1.1 mmol) in ethanol-water at 0° C., was slowly added. The solution was allowed to rise to room temperature and was stirred for a further 12 h. The (triethylphosphine)(sporopollenin —S)gold(I) derivative (0.8 mmol/g) was washed with water, ethanol and ether and dried.

The invention claimed is:

1. A pharmaceutical or dietetic dosage form comprising an effective quantity of an active substance chemically or physically bound to, or encapsulated within, a support selected from: an exine coating of spores of a plant, moss, fungus, bacterium or algae or a fragment thereof, wherein:
   the active substance comprises one or more drugs, one or more dietetic substances, or a mixture thereof;
   the coating comprises sporopollenin derived from plant, moss, fungus, bacterium or algae spores;
   the dosage form is in the form of a foodstuff or a pharmaceutical selected from the group consisting of a tablet, a capsule, a soft gel capsule, an ovule, an elixir, granules, an inhaleable formulation comprising an inhaleable carrier, a suppository, a pessary, a gel, a hydrogel lotion, a cream, an ointment, a dusting powder and a skin patch; and
   any spore protein present in the dosage form is present at less than 0.5% of the exine coating.

2. A dosage form as claimed in claim 1 which is adapted for administration orally, buccally, sublingually or transdermally.

3. A dosage form as claimed in claim 1 which is adapted for intra-nasal or pulmonary administration.

4. A dosage form as claimed in claim 1 wherein the support has a particle size in the range about 1-100 microns.

5. A dosage form as claimed in claim 4 wherein the support has a particle size in the range about 1-30 microns.

6. A dosage form as claimed in claim 5 wherein the support has a particle size in the range about 1-10 microns.

7. A dosage form as claimed in claim 1 wherein the active substance comprises a peptide or genetic material.

8. A dosage form as claimed in claim 1 wherein the exine coating is functionalised.

9. A dosage form as claimed in claim 1 wherein the active substance is either base or acid labile.

10. A dosage form as claimed in claim 1 wherein the active substance is a metal.

11. A dosage form as claimed in claim 1 wherein the outside of the exine coating is further coated with a material to aid retention of the active substance.

12. A dosage form as claimed in claim 1 wherein the active substance is absorbed on the surface of the support.

13. dosage form as claimed in claim 1 wherein the exine coating contains a sufficiently low level of spore protein that further loss of protein is not observed following reflux of the exine coating for 2 hours in 6% w/v aqueous potassium hydroxide.

14. A dosage form as claimed in claim 1 wherein the active substance is encapsulated within a cavity within a wall of the exine coating, or within its central cavity.

15. A dosage form as claimed in claim 14 wherein the active substance is encapsulated within the central cavity of the exine coating.

16. A dosage form as claimed in claim 1 wherein the exine coating comprises less than 0.1% spore protein.

17. A dosage form as claimed in claim 1 wherein the active substance comprises a substance selected from the group consisting of a vitamin, mineral, essential oil, or food flavoring.

18. A dosage form as claimed in claim 1 wherein the exine coating is derived from a *Lycopodium* spore.

19. A dosage form as claimed in claim 18 wherein the exine coating is derived from a *Lycopodium clavatum* spore.

20. A dosage form as claimed in claim 1 wherein the dosage form is in the form of a tablet.

21. A dosage form as claimed in claim 1 wherein the dosage form is in the form of a capsule.

22. A dosage form as claimed in claim 1 wherein the dosage form is in the form of a soft gel capsule.

23. A dosage form as claimed in claim 1 wherein the dosage form is in the form of an ovule.

24. A dosage form as claimed in claim 1 wherein the dosage form is in the form of an elixir.

25. A dosage form as claimed in claim 1 wherein the dosage form is in the form of granules.

26. A dosage form as claimed in claim 1 wherein the dosage form is in the form of an inhaleable formulation comprising an inhaleable carrier.

27. A dosage form as claimed in claim 1 wherein the dosage form is in the form of a suppository.

28. A dosage form as claimed in claim 1 wherein the dosage form is in the form of a pessary.

29. A dosage form as claimed in claim 1 wherein the dosage form is in the form of a gel.

30. A dosage form as claimed in claim 1 wherein the dosage form is in the form of a hydrogel lotion.

31. A dosage form as claimed in claim 1 wherein the dosage form is in the form of a cream.

32. A dosage form as claimed in claim 1 wherein the dosage form is in the form of an ointment.

33. A dosage form as claimed in claim 1 wherein the dosage form is in the form of a dusting powder.

34. A dosage form as claimed in claim 1 wherein the dosage form is in the form of a skin patch.

35. A pharmaceutical or dietetic dosage form comprising an effective quantity of an active substance chemically or physically bound to, or encapsulated within, a support selected from: an exine coating of spores of a plant, moss, fungus, bacterium or algae or a fragment thereof, wherein:
   the active substance comprises one or more drugs, one or more dietetic substances, or a mixture thereof;
   the coating comprises sporopollenin derived from plant, moss, fungus, bacterium or algae spores;
   the dosage form is in the form of a foodstuff or a pharmaceutical selected from the group consisting of a tablet, a capsule, a soft gel capsule, an ovule, an elixir, granules, an inhaleable formulation comprising an inhaleable carrier, a suppository, a pessary, a gel, a hydrogel lotion, a cream, an ointment, a dusting powder and a skin patch; and
   the exine coating is obtainable by a process comprising treating a spore with a solvent, an alkali and an acid and is formulated without additional spore protein.

36. A dosage form as claimed in claim 35 which is adapted for administration orally, buccally, sublingually or transdermally.

37. A dosage form as claimed in claim 36 wherein the support has a particle size in the range about 1-30 microns.

38. A dosage form as claimed in claim 35 which is adapted for intra-nasal or pulmonary administration.

39. A dosage form as claimed in claim 38 wherein the support has a particle size in the range about 1-10 microns.

40. A dosage form as claimed in claim 35 wherein the support has a particle size in the range about 1-100 microns.

41. A dosage form as claimed in claim 35 wherein the active substance comprises a peptide or genetic material.

42. A dosage form as claimed in claim 35 wherein the exine coating is functionalised.

43. A dosage form as claimed in claim 35 wherein the active substance is either base or acid labile.

44. A dosage form as claimed in claim 35 wherein the active substance is a metal.

45. A dosage form as claimed in claim 35 wherein the outside of the exine coating is further coated with a material to aid retention of the active substance.

46. A dosage form as claimed in claim 35 wherein the active substance is absorbed on the surface of the support.

47. A dosage form as claimed in claim 35 wherein the exine coating contains a sufficiently low level of spore protein that further loss of protein is not observed following reflux of the exine coating for 2 hours in 6% w/v aqueous potassium hydroxide.

48. A dosage form as claimed in claim 35 wherein the active substance is encapsulated within a cavity within a wall of the exine coating, or within its central cavity.

49. A dosage form as claimed in claim 48 wherein the active substance is encapsulated within the central cavity of the exine coating.

50. A dosage form as claimed in claim 35 wherein the exine coating comprises less than 0.1% spore protein.

51. A dosage form as claimed in claim 50 wherein the exine coating is derived from a *Lycopodium clavatum* spore.

52. A dosage form as claimed in claim 35 wherein the active substance comprises a substance selected from the group consisting of a vitamin, mineral, essential oil, or food flavoring.

53. A dosage form as claimed in claim 35 wherein the exine coating is derived from a *Lycopodium* spore.

54. A dosage form as claimed in claim 35 wherein the dosage form is in the form of a tablet.

55. A dosage form as claimed in claim 35 wherein the dosage form is in the form of a capsule.

56. A dosage form as claimed in claim 35 wherein the dosage form is in the form of a soft gel capsule.

57. A dosage form as claimed in claim 35 wherein the dosage form is in the form of an ovule.

58. A dosage form as claimed in claim 35 wherein the dosage form is in the form of an elixir.

59. A dosage form as claimed in claim 35 wherein the dosage form is in the form of granules.

60. A dosage form as claimed in claim 35 wherein the dosage form is in the form of an inhaleable formulation comprising an inhaleable carrier.

61. A dosage form as claimed in claim 35 wherein the dosage form is in the form of a suppository.

62. A dosage form as claimed in claim 35 wherein the dosage form is in the form of a pessary.

63. A dosage form as claimed in claim 35 wherein the dosage form is in the form of a gel.

64. A dosage form as claimed in claim 35 wherein the dosage form is in the form of a hydrogel lotion.

65. A dosage form as claimed in claim 35 wherein the dosage form is in the form of a cream.

66. A dosage form as claimed in claim 35 wherein the dosage form is in the form of an ointment.

67. A dosage form as claimed in claim 35 wherein the dosage form is in the form of a dusting powder.

68. A dosage form as claimed in claim 35 wherein the dosage form is in the form of a skin patch.

69. A pharmaceutical or dietetic dosage form comprising an effective quantity of an active substance chemically or physically bound to, or encapsulated within, a support selected from: an exine coating of spores of a plant, moss, fungus, bacterium or algae or a fragment thereof, wherein:

the active substance comprises one or more drugs, one or more dietetic substances, or a mixture thereof;

the coating comprises sporopollenin derived from plant, moss, fungus, bacterium or algae spores;

the dosage form is in the form of a foodstuff or a pharmaceutical comprising an ingredient selected from the group consisting of a flavor, a preservative, an antioxidant, a disintegrant, and an effervescent couple; and any spore protein present in the dosage form is present at less than 0.5% of the exine coating.

70. A dosage form as claimed in claim 69, wherein the ingredient comprises a flavor.

71. A dosage form as claimed in claim 69, wherein the ingredient comprises a preservative.

72. A dosage form as claimed in claim 69, wherein the ingredient comprises an antioxidant.

73. A dosage form as claimed in claim 69, wherein the ingredient comprises a disintegrant.

74. A dosage form as claimed in claim 69, wherein the ingredient comprises an effervescent couple.

75. A pharmaceutical or dietetic dosage form comprising an effective quantity of an active substance chemically or physically bound to, or encapsulated within, a support selected from: an exine coating of spores of a plant, moss, fungus, bacterium or algae or a fragment thereof, wherein:

the active substance comprises one or more drugs. one or more dietetic substances, or a mixture thereof;

the coating comprises sporopollenin derived from plant, moss, fungus, bacterium or algae spores;

the dosage form is in the form of a foodstuff or a pharmaceutical comprising an ingredient selected from the group consisting of a flavor, a preservative, an antioxidant, a disintegrant, and an effervescent couple; and the exine coating is obtainable by a process comprising treating a spore with a solvent, an alkali and an acid and is formulated without additional spore protein.

76. A dosage form as claimed in claim 75, wherein the ingredient comprises a flavor.

77. A dosage form as claimed in claim 75, wherein the ingredient comprises a preservative.

78. A dosage form as claimed in claim 75, wherein the ingredient comprises an antioxidant.

79. A dosage form as claimed in claim 75, wherein the ingredient comprises a disintegrant.

80. A dosage form as claimed in claim 75, wherein the ingredient comprises an effervescent couple.

81. A dosage form as claimed in claims 69 or 75, wherein the dosage form comprises, or is present in, a food.

82. A dosage form as claimed in claims 69 or 75, wherein the dosage form comprises, or is present in, a drink.

* * * * *

UNITED STATES PATENT AND TRADEMARK OFFICE
CERTIFICATE OF CORRECTION

PATENT NO. : 7,608,270 B2　　　　　　　　　　　　　　　　　　　　　　Page 1 of 1
APPLICATION NO. : 10/877042
DATED : October 27, 2009
INVENTOR(S) : Beckett et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 497 days.

Signed and Sealed this

Twelfth Day of October, 2010

David J. Kappos
*Director of the United States Patent and Trademark Office*